United States Patent
Behar et al.

(10) Patent No.: US 8,016,163 B2
(45) Date of Patent: Sep. 13, 2011

(54) FLUID DISPENSER HEAD

(75) Inventors: Alain Behar, Suresnes (FR); Laurent Decottignies, Cergy (FR)

(73) Assignee: Airlessystems, Charleval (FR)

( * ) Notice: Subject to any disclaimer, the term of this patent is extended or adjusted under 35 U.S.C. 154(b) by 958 days.

(21) Appl. No.: 10/574,836

(22) PCT Filed: Oct. 6, 2004

(86) PCT No.: PCT/FR2004/050490
§ 371 (c)(1), (2), (4) Date: Aug. 9, 2006

(87) PCT Pub. No.: WO2005/032973
PCT Pub. Date: Apr. 14, 2005

(65) Prior Publication Data
US 2007/0075097 A1    Apr. 5, 2007

(30) Foreign Application Priority Data
Oct. 9, 2003   (FR) ...................................... 03 11822

(51) Int. Cl.
*G01F 11/00* (2006.01)
(52) U.S. Cl. ...................... 222/256; 222/257; 222/402.1
(58) Field of Classification Search .................. 222/256, 222/257, 394, 402.13, 402.21, 518, 494, 222/402.1, 513, 321.7, 321.1–321.6, 321.8, 222/321.9; 239/343; D9/448; 401/190
See application file for complete search history.

(56) References Cited

U.S. PATENT DOCUMENTS

| | | | |
|---|---|---|---|
| 2,670,871 A * | 3/1954 | Spiess, Jr. et al. ............ 220/789 |
| 2,856,104 A * | 10/1958 | Spiess, Jr. et al. ....... 222/402.25 |
| 2,908,479 A * | 10/1959 | Goodspeed, Jr. ............. 251/320 |
| 3,096,002 A * | 7/1963 | Focht ....................... 222/402.15 |
| 3,317,092 A | 5/1967 | Jurasek |
| 3,361,301 A * | 1/1968 | Meshberg ...................... 222/149 |
| 3,428,223 A * | 2/1969 | Lewiecki et al. ......... 222/402.12 |
| 4,775,081 A * | 10/1988 | Morane ..................... 222/402.13 |
| 4,860,933 A * | 8/1989 | Morane et al. ........... 222/402.13 |
| 4,901,891 A * | 2/1990 | Goncalves ................ 222/402.13 |
| 4,969,584 A * | 11/1990 | Joulia ....................... 222/402.11 |
| 5,340,031 A * | 8/1994 | Neuhaus et al. .............. 239/343 |
| 5,765,601 A * | 6/1998 | Wells et al. ..................... 141/38 |
| 5,915,599 A * | 6/1999 | Takahashi ................ 222/402.13 |
| 6,202,899 B1 * | 3/2001 | Lasserre et al. ............. 222/402.1 |
| 7,097,078 B2 * | 8/2006 | Sanchez .................... 222/402.21 |
| D537,714 S * | 3/2007 | Yerby et al. .................... D9/448 |
| 2003/0071085 A1 * | 4/2003 | Lasserre et al. .......... 222/402.13 |

FOREIGN PATENT DOCUMENTS

| | | |
|---|---|---|
| DE | 79 01 179 U1 | 11/1981 |
| DE | 40 02 817 A1 | 8/1991 |
| DE | 4002817 A1 * | 8/1991 |
| FR | 2 453 790 A | 11/1980 |

* cited by examiner

*Primary Examiner* — Kevin P Shaver
*Assistant Examiner* — Jonathan Wood
(74) *Attorney, Agent, or Firm* — Sughrue Mion, PLLC

(57) ABSTRACT

A fluid dispenser head for mounting on an actuator rod of a dispenser member that is displaceable down and up along an axis (X), the head including an axial connection sleeve for engaging on the actuator rod and defining an inlet duct, the head further including a dispenser endpiece defining an endpiece channel that is connected to the inlet duct via a connection channel, the endpiece including a free dispenser end defining a dispenser orifice that is situated at a downstream end of the endpiece channel, the head further including a bearing surface on which axial pressure can be exerted so as to drive in the actuator rod, where the endpiece extends substantially parallel to the axis (X), and is offset away from the axis.

17 Claims, 2 Drawing Sheets

FLUID DISPENSER HEAD

BACKGROUND OF THE INVENTION (1) Field of the Invention

The present invention relates to a fluid dispenser head for mounting on, or for associating with, an actuator rod of a dispenser member that is displaceable down and up along a longitudinal displacement axis. The rod internally defines a flow channel through which the fluid is delivered to the dispenser head. The dispenser member can be in the form of a pump or a valve including a body inside which the actuator rod is mounted so as to be displaced down and up against the action of a return spring that tends to return the actuator rod into a rest position. The dispenser head is thus associated with a pump or a valve so as to constitute a fluid dispenser that is also provided with a fluid reservoir from which the pump or the valve takes the fluid so as to be dispensed through the head. Such dispenser heads are frequently used in the fields of perfumery, cosmetics, or even pharmacy.

(2) Description of Related Art

In general, such dispenser heads comprise an axial connection sleeve for engaging on the free end of the actuator rod. In addition, the head further comprises a dispenser endpiece defining an endpiece channel that is connected to the inlet duct via a connection channel. The endpiece includes a free dispenser end defining a dispenser orifice that is situated at a downstream end of the endpiece channel. The head further comprises a bearing surface on which axial pressure can be exerted so as to drive in the actuator rod. The dispenser head therefore fulfils both a pushbutton function and a dispensing function. That type of dispenser head is already known in the prior art. It includes a dispenser endpiece that slops relative to the longitudinal displacement axis. As a result of the slope of the dispenser endpiece, the dispenser head is difficult to manufacture: given that the head is made by molding, the slope of the endpiece requires a relatively complicated mold that is not displaceable along a single axis.

BRIEF SUMMARY OF PREFERRED EMBODIMENTS OF THE INVENTION

An object of the present invention is to simplify the manufacture of such a dispenser head. Another object of the invention is to provide the dispenser head with an applicator function for applying fluid to an application surface. Another object is to guarantee preservation of the fluid inside the head, even in the proximity of the dispenser orifice. Another object is to simplify the assembly of such a dispenser head. Another object is to make the dispenser head with as few component parts as possible.

In order to achieve these objects, the present invention proposes that the endpiece extends substantially parallel to the longitudinal displacement axis of the actuator rod, and is offset away from the axis. Because the endpiece extends parallel to the axis, the dispenser head is easier both to mold and to assemble. The bearing surface can advantageously extend axially downstream from the connection sleeve, intersecting said axis. By offsetting the endpiece, it is possible to release a relatively large bearing surface, making it possible to apply a completely centered bearing force since the force acts on and along the longitudinal actuation axis.

In another advantageous aspect of the invention, the dispenser head may further comprise a base skirt that extends around the connection sleeve, the endpiece being inscribed within the outline of the skirt. Advantageously, the endpiece is axially tangential to said skirt. This signifies that the skirt defines the radial outer limit of the dispenser head. In other words, this also signifies that the dispenser endpiece does not extend radially beyond the periphery of the skirt.

According to another advantageous characteristic of the invention, the dispenser head may comprise a substantially rigid inner core, and a substantially flexible outer casing, said core being engaged in said casing. Advantageously, the core is received axially in the casing. It should be noted that this characteristic of designing the dispenser head made up of a core and of a casing can be implemented independently of the fact that the endpiece extends parallel to the axis, and is offset therefrom. The substantially rigid core constitutes a solid structure for engaging on the actuator rod. The flexible casing makes it possible to perform functions that require its material to deform.

In an advantageous embodiment, the core forms the connection sleeve, part of the connection channel, and advantageously part of a bottom portion of the endpiece channel. In addition, the casing may form the dispenser endpiece, and a bearing wall defining the bearing surface. The core advantageously forms an axial spout that is engaged in the endpiece, a bottom portion of the endpiece channel being formed between the casing and the spout. The spout advantageously includes an axial groove that co-operates with the dispenser endpiece to form the bottom portion of the endpiece channel. The spout preferably includes a top end that terminates in a position set back from the dispenser orifice, a top portion of the endpiece channel being formed solely by the flexible casing downstream from the spout, such that the endpiece is flexible at the top portion.

In another aspect of the invention, the core forms a bearing plate into which the duct opens out axially, the connection channel being formed between the plate and the casing. The plate advantageously includes a transverse and non-axial groove that co-operates with the casing to form the connection channel.

In another aspect of the invention, the core forms a collar that is engaged in a base skirt formed by the casing. Here also, the core makes it possible to impart a certain amount of strength to the flexible casing.

According to another characteristic of the invention that can be implemented independently of the others, the dispenser endpiece may present a flat spatula shape. The dispenser endpiece thus fulfills two functions, namely both a dispensing function and a fluid-applicator function. The flat spatula shape makes it possible to spread the fluid easily on any application surface.

According to another advantageous characteristic, the dispenser orifice may be formed by a self-sealing flexible slot. This is made possible because the casing is made of an elastically-deformable flexible material. The self-sealing flexible slot thus defines two lips for coming into leaktight contact with each other when no pressure exists inside the dispenser endpiece. A dispenser orifice is thus made integrally with the remainder of the flexible casing, whereas, in the prior art, the dispenser orifice is often formed by a nozzle that is fitted onto another element of the head.

In a practical embodiment, the bearing surface may slope, forming an angle lying in the range 40° to 90° relative to the axis, in such a manner as to intersect the axis. The slope of the bearing surface makes it possible to extend the area of the surface, and simultaneously make the surface more ergonomic.

According to another characteristic that can be implemented independently of the other characteristics, the dispenser endpiece may be flexible, at least in part, in particular at its free end. It is clearly possible to envisage a dispenser head that does not have an axially-offset endpiece, but that defines a flexible end portion that also forms the dispenser orifice. The head can thus include an endpiece that is flexible in part, defining a self-sealing dispenser slot, and that makes it possible, once the fluid has been dispensed, to apply or spread the fluid by means of the flexible portion of the endpiece.

BRIEF DESCRIPTION OF THE DRAWINGS

The invention is described more fully below with reference to the accompanying drawings which show an embodiment of the invention by way of non-limiting example. In the figures.

DETAILED DESCRIPTION OF THE PREFERRED EMBODIMENTS

Figure 1:
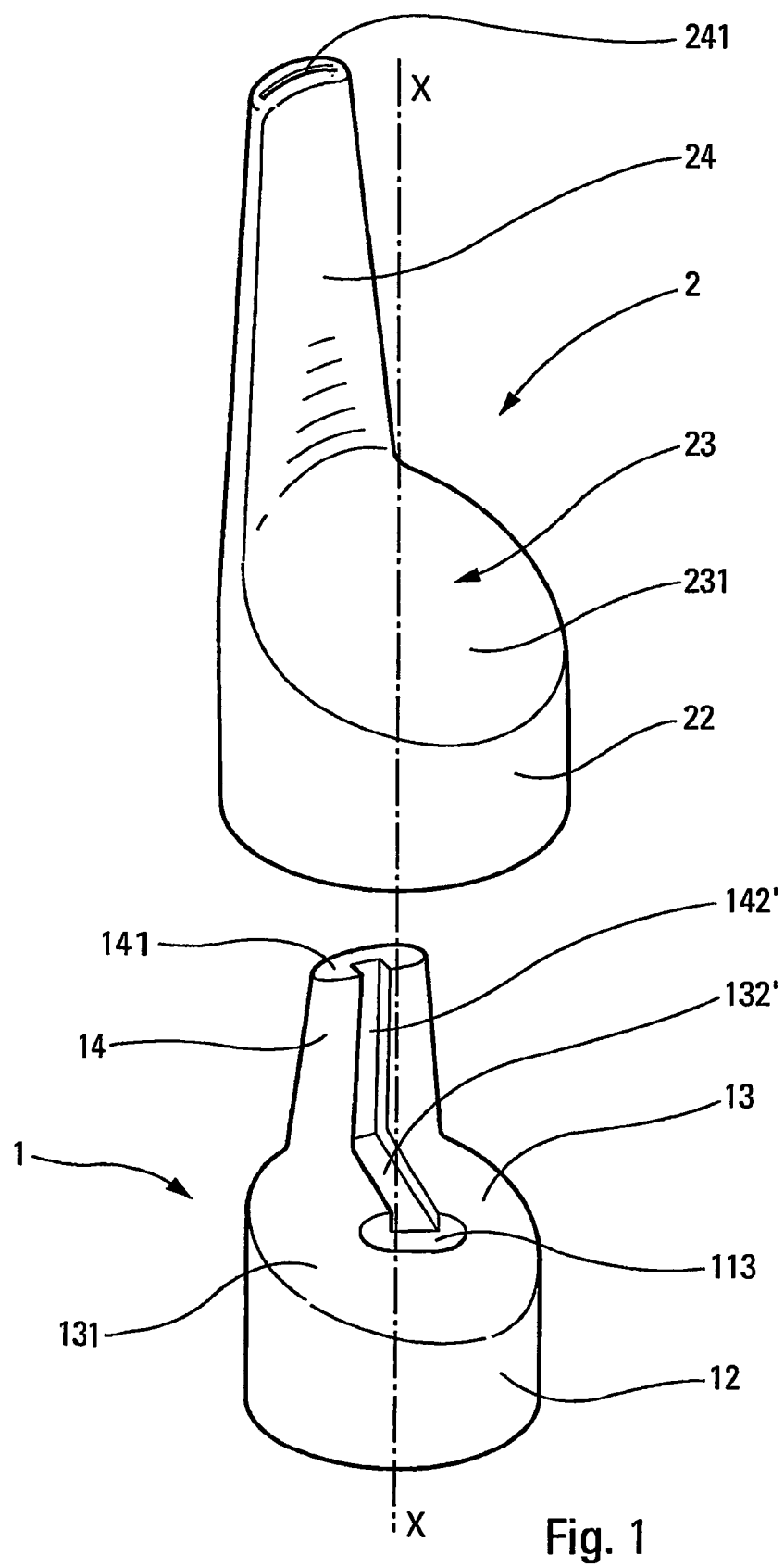
FIG. 1 is a perspective view, exploded along the axis X, and showing a dispenser head constituting an embodiment of the invention.

The embodiment described by way of example of a fluid dispenser head of the invention is a head of the pushbutton type that is pressed in order to dispense the fluid. The dispenser head is mounted on, or associated with, a dispenser member that can be a pump or a valve. In the drawings, the dispenser member is designated by the numerical reference 3. The dispenser head is designated by the numerical references 1 and 2, since it is constituted by two distinct elements, namely a core 1, and a casing 2.

Figure 2:
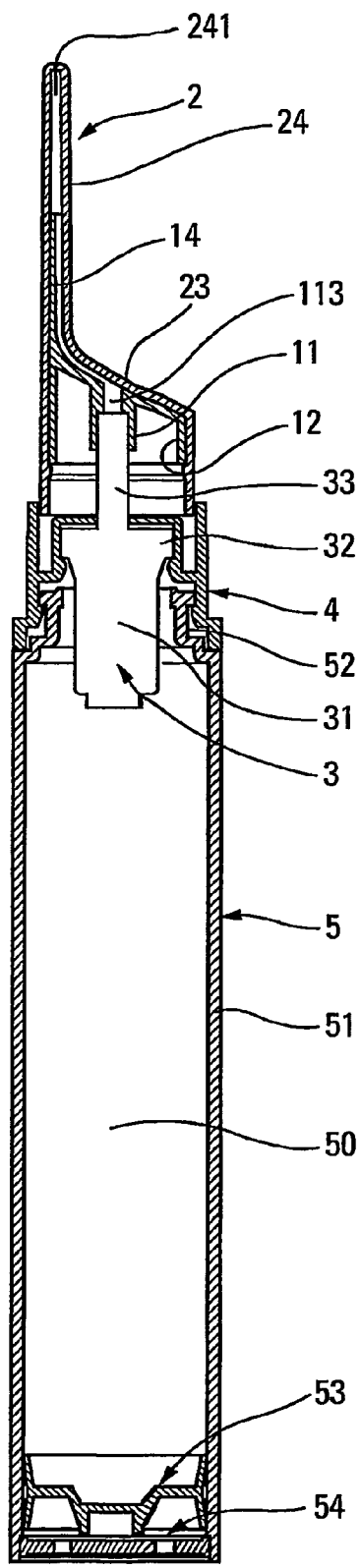
FIG. 2 is a vertical section view through a fluid dispenser fitted with the FIG. 1 dispenser head.
Figure 3:
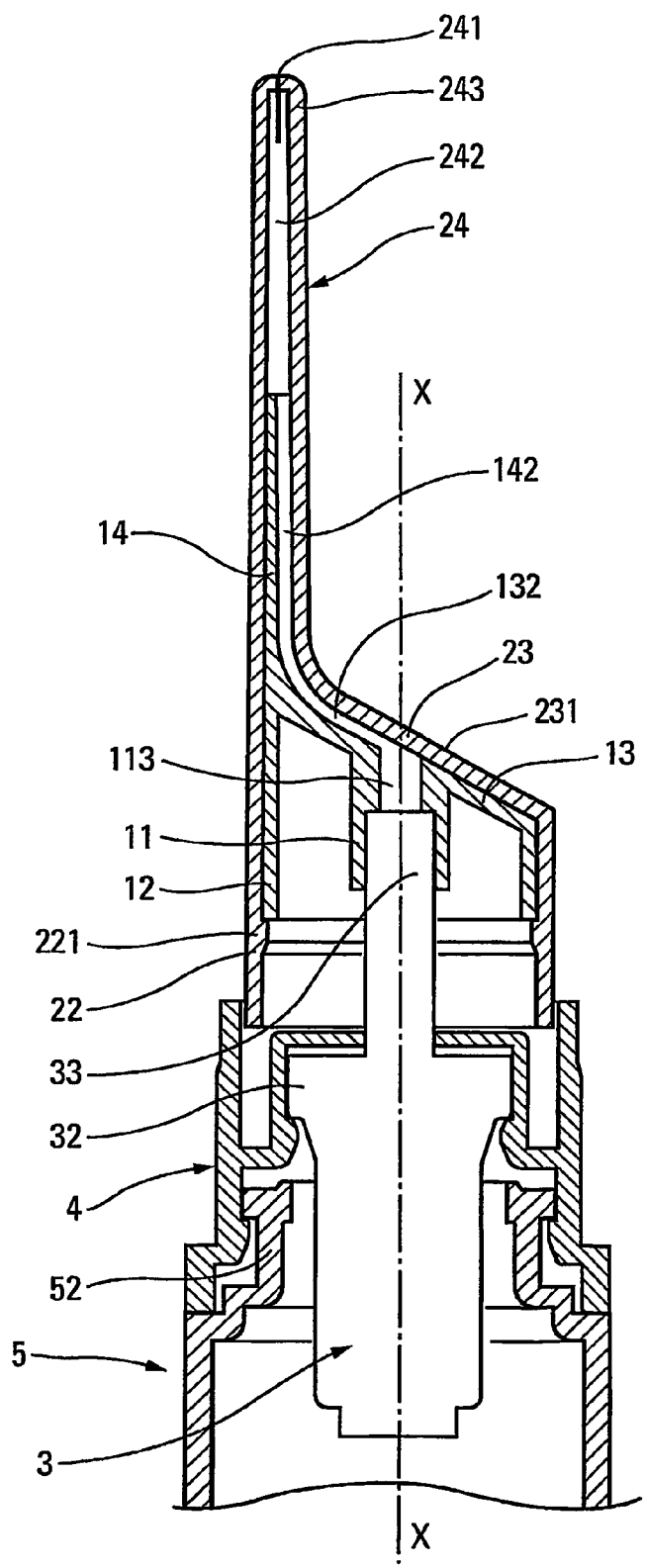
FIG. 3 is a larger-scale view of the top portion of the FIG. 2 dispenser, integrating the dispenser head of the invention.

The dispenser member 3 comprises a body 31 forming a collar 32 that is engaged in a fastener ring 4. The dispenser member 3 also comprises an actuator rod 33 that is mounted to be displaced down and up inside the body 31. The actuator rod 33 is urged into its rest position by a return spring (not shown). In FIGS. 2 and 3, the actuator rod is in its rest position. The actuator rod defines an internal flow channel through which there flows the fluid that is put under pressure in the pump body 31, so as to be dispensed through the dispenser head. The rod extends and is displaced along a longitudinal actuation axis X that can coincide with the axes of symmetry of the receptacle, of the ring, and of the body of the dispenser member.

The fastener ring 4 that is engaged with the body 31 of the dispenser member 3 is fastened on the neck 52 of a receptacle 5 defining an internal reservoir 50. The receptacle 5 comprises a substantially cylindrical tube 51 inside which a follower-piston or scraper 53 can slide. Optionally, a separate bottom 54 can close the bottom end of the tube 51. That is one particular kind of receptacle, in which the internal volume of the reservoir 50 decreases as the fluid is dispensed by the dispenser member. However, other types of receptacle, having fixed or variable capacity, can be used in the context of the invention.

The type of dispenser member, of fastener ring, and of receptacle is not critical to the present invention. It suffices for the dispenser member to be provided with an actuator rod that is displaceable down and up, and that defines an internal flow duct.

The dispenser head in this particular non-limiting embodiment of the invention therefore comprises a core 1, and a casing 2. The core 1 is made of a substantially rigid material, whereas the casing 2 is made of a relatively flexible and elastically-deformable material. The core and the casing can be made of conventional plastics materials, such as polyethylene, polypropylene, and elastomer thermoplastics. Making the dispenser head both from a core and from a casing should not be considered as limiting. A dispenser head of the invention could also be made as a single part, or it could even be made of more than two parts. However, in the embodiment shown in the drawings, the head comprises both a core and a casing.

The core 1 is preferably made as a single part by injection-molding plastics material. The core 1 includes a substantially cylindrical collar 12 having a section that is preferably circular. The collar 12 is closed at its top end by a bearing plate 13 that extends in sloping manner relative to the axis of the cylinder formed by the collar 12. In addition, the axis of the cylinder 12 coincides with the longitudinal actuation axis X of the actuator rod 33. At its highest portion, the bearing plate 13 is provided with a spout 14 that projects axially upwards along the axis X, but is offset away from the axis. The spout 14 extends upwards in register with the outer wall of the collar 12, as can be seen clearly in FIG. 3. The spout presents a top end 141. In addition, on its face facing the axis X, the spout is formed with an axial groove 142' having a bottom end that is connected to another groove 132' that is formed in the thickness of the bearing plate 13 and that extends transversely and non-axially. The two grooves 132' and 142' therefore extend each other by forming an angle at the base of the spout 14 that is connected to the plate 13. The bottom end of the non-axial groove 132' opens out into a duct 113 that passes through the thickness of the plate 13.

The plate 13 thus defines a top surface 131 that is relatively or completely plane, except where the non-axial groove 132' and the duct 113 are formed. The core 1 also forms a connection sleeve 11 that internally forms the inlet duct 113. The sleeve 11 is generally cylindrical in shape, with a cylinder axis that coincides with the axis X of the actuator rod once the dispenser head is mounted on the actuator rod.

The casing 2 is preferably made as a single part from a molded plastics material, such as elastomer thermoplastic. The casing 2 includes a skirt 22 that is substantially circularly cylindrical. The skirt 22 also extends along the axis X, once it is mounted on the rod. The skirt 22 is closed at its top end by a bearing plate 23 that forms an outer bearing surface 231. The wall 23 extends in sloping manner relative to the axis X. The angle of slope of the wall 23 relative to the axis X can lie in the range 40° to 90° relative to the axis X, i.e. relative to the vertical. In other words, the bearing wall 23 can be horizontal, or even relatively steeply sloping. Naturally, the steeper the slope, the more the area of the wall 23 increases. The bearing surface 231 is for applying a bearing force by means of one or more fingers of the hand. The greater the area, the easier it is to apply one or more fingers. However, it should be observed that the bearing surface 231 is situated in central manner on the axis X. The bearing wall 23 is situated axially downstream from the axial inlet duct 113. In other words, the bearing wall 23 intersects the axis X. The bearing force exerted by the finger of the user is therefore applied directly along the axis X, thereby making it possible to guarantee good distribution of the bearing force on the head during dispensing. Although it is made of flexible material, the bearing wall 23 cannot deform, given that it is in contact with the bearing plate 13 formed by the rigid core 1. The bearing wall 23 also covers the duct 113 and the non-axial groove 132' without blocking them. In contrast, the bottom surface of the bearing wall 23 comes to complete the non-axial groove 132', so as to form a connection channel 132 that can be seen in FIG. 3. In addition, the bottom surface of the bearing wall 23 forms a deflection wall at the outlet from the axial inlet duct 113, so as to make it possible to deflect the fluid from the duct 113 into the connection channel 132. It should also be noted that the connection channel 132 is relatively leaktight, even though the bearing wall 23 is not fastened or bonded to the plate 13. During dispensing, the user exerts pressure on the bearing surface 231, and that tends to press the wall 23 hard against the plate 13. Thus, the outlet from the duct 113, and the connection channel 132 are completely isolated. The relatively flexible material of the bearing wall 23 also contributes to isolating the connection channel 132.

At is highest point, the bearing wall 23 forms a dispenser endpiece 24 that projects axially upwards, and is offset away from the axis X. The dispenser endpiece 24 extends in axial and offset manner, i.e. parallel to the axis X. In particular, it can be seen in FIGS. 2 and 3 that the dispenser endpiece 24 extends in offset manner in register with the tangent or the edge of the skirt 22: the outer wall of the endpiece 24 is completely in alignment with the outer wall of the skirt 22 on the left-hand portion, as can be seen in FIGS. 2 and 3. It should also be observed that the endpiece 24 is inscribed within the outline of the skirt 22. In other words, the endpiece 24 does not project radially outwards relative to the skirt 22 when the casing is observed from above or from below along the axis X. This is a characteristic that can be protected regardless of whether or not the dispenser head is made of two parts. In particular, it is possible to imagine a dispenser head forming both a bearing surface, and an axially-offset dispenser endpiece that lies within or that is inscribed within the outline of the base skirt of the dispenser head. As a result of the endpiece extending in axial manner, it is easy to mold, to unmold, and to assemble the part. The inside of the dispenser head can be molded using a single mold core. In addition, the dispenser head can be made as a single part. When the head is made of two parts, i.e. with a core 1 and a casing 2, as in the embodiment shown in the figures, the axial orientation of the endpiece inscribed within the outline of the skirt also makes it easy and simple to assemble the core 1 inside the casing 2. Assembly can be performed by engaging the core 1 in the casing 2 in completely axial manner. The rigid collar 12 becomes engaged inside the skirt 22, whereas the plate 13 comes into contact with the bearing wall 23. In addition, the spout 14 penetrates into the endpiece 24. As mentioned above, the bearing wall 23 comes to complete the connection channel 132 formed by the groove 132' formed in the plate 13. In addition, the endpiece 24 comes to complete the axial groove 142' formed in the spout 14, in such a manner as to form the bottom portion 142 of a endpiece channel that extends inside the endpiece 24. The bottom portion 142 of the endpiece channel terminates at the top end 141 of the spout 14. Beyond the end 141, the endpiece 24 forms a top portion 242 of the endpiece channel that extends until it reaches a downstream end forming a dispenser orifice 241 in the form of a self-sealing slot. Thus, the entire free end portion 243 of the endpiece 24, formed solely by the endpiece 24, presents an elastically-deformable characteristic that can be likened to that of a flexible spatula. In addition, the endpiece 24 presents a flat spatula shape, as can be seen in FIG. 1. The endpiece 24 is wider circumferentially than it is radially. This can be seen clearly by comparing FIG. 1 with FIG. 3. Making a dispenser endpiece flexible, at least in part, with a dispenser orifice, e.g. in the form of a self-sealing slot, is a characteristic that can be implemented regardless of whether or not the endpiece extends in axially offset manner, and regardless of whether or not the head is made both from a core and from a casing. It is clearly possible to envisage a dispenser head forming a transverse or horizontal endpiece having a free end portion that is flexible, and that forms a separate or integral dispenser orifice. When the dispenser orifice is made in the form of a self-sealing slot 241, the slot can be made easily by making an incision in the end of the endpiece 24 by means of a blade. A slot is thus formed that is constituted by two lips that come into mutual leaktight contact when no pressure exists inside the endpiece channel. This type of dispenser orifice simultaneously performs a closure function making it possible to protect the fluid inside the endpiece 24 from the outside air.

In contrast, it is also possible to envisage the spout 14 extending as far as the dispenser orifice 241. In this event, the endpiece 24 is elastically deformable to a smaller extent, if at all.

By making the endpiece 24 in the form of a flat spatula that is advantageously elastically deformable, it is possible to use the endpiece as a fluid applicator for applying and/or spreading the fluid on an application surface.

Furthermore, the completely or substantially axially-offset orientation of the endpiece 24, advantageously with a bearing surface that is completely centered on the axis, makes it possible to obtain good positioning accuracy in dispensing and applying the fluid on an application surface.

Such a dispenser head constituted by a core 1 and a casing 2 is very simple to assemble, since it suffices to insert the rigid core 1 axially into the flexible casing 2. This is possible since the spout 14 and the endpiece 24 extend in axial manner. The spout 14 penetrates into the endpiece 24 so as to form the bottom portion 142 of the endpiece channel, the plate 13 comes into contact with the wall 23 so as to form the connection channel 132, and the collar 12 becomes engaged in the skirt 22. A snap-fastener profile 221 can even be provided on the inside wall of the skirt 22, so as to guarantee that the collar 12 is held in stable and permanent manner in the casing 2.

Various modifications are possible, without however going beyond the ambit of the invention. The spout 14 could be longer or shorter. The same applies for the endpiece 24. The spout 14 could form solely the connection channel 132, without forming a portion of the endpiece channel. The spout 14 could also form the entire endpiece channel. By way of example, it is possible to envisage the bottom portion 142 of the endpiece channel formed completely inside the spout 14. It is thus possible to envisage dispenser orifices of types other than in the form of a self-sealing slot. A permanently-open dispenser orifice could be envisaged. A completely horizontal bearing surface could also be envisaged. Manufacturing the dispenser head as a single part or by dual injection could also be envisaged. In particular, it is possible to envisage overmolding the casing on the core, providing certain conventional precautions are taken.

It is also advantageous for the bottom end of the skirt 22 to extend inside a bushing formed by the fastener ring 4. Thus, the actuator rod 33 is not visible.

The invention claimed is:

1. A cosmetic product dispenser head for mounting on an actuator rod (33) of a pump (3) that is displaceable down and up along a central axis (X) of the actuator rod, said head comprising an axial connection sleeve (11) for engaging on the actuator rod (33) and defining an inlet duct (113), said head further comprising a dispenser endpiece (24) defining an endpiece channel (142, 242) that is connected to the inlet duct (113) via a connection channel (132), said endpiece (24) including a dispenser orifice (241) that is situated at a downstream end of the endpiece channel, said head further comprising a bearing surface (231) on which axial pressure can be exerted so as to drive in the actuator rod (33), the endpiece (24) extending substantially parallel to said central axis (X), and being offset away from the central axis, the bearing surface (231) located axially downstream from the connection sleeve (11), intersecting said central axis (X), the head further comprising a base skirt (22) that extends around the connection sleeve (11), the endpiece (24) being inscribed within the outline of the skirt, the endpiece (24) being axially tangential to said skirt (22);

the cosmetic product dispenser head further comprising an inner core (1), and an outer casing (2), said core being entirely engaged in said casing, the core (1) being received axially along the central axis (X) in the casing (2), the core (1) forming the connection sleeve (11) and part of the connection channel (132), the casing (2) forming the base skirt (22), the dispenser endpiece (24) and a bearing wall (23) defining the bearing surface (231).

2. A dispenser head according to claim 1, in which the core (1) forms an axial spout (14) that is engaged in the endpiece (24), a bottom portion (142) of the endpiece channel being formed between the casing (2) and the spout (14).

3. A dispenser head according to claim 2, in which the spout (14) includes an axial groove (142') that co-operates with the dispenser endpiece (24) to form the bottom portion (142) of the endpiece channel.

4. A dispenser head according to claim 2, in which the spout (14) includes an end (141) that terminates in a position set back from the dispenser orifice (241), a top portion (242) of the endpiece channel being formed solely by the casing (2) downstream from the spout, wherein the casing is flexible such that the endpiece is flexible at the top portion, the dispenser orifice (241) being formed in the top portion.

5. A dispenser head according to claim 1, in which the core (1) forms a bearing plate (13) into which the duct (113) opens out axially, the connection channel (132) being formed between the plate (13) and the casing (2).

6. A dispenser head according to claim 5, in which the plate (13) includes a transverse groove (132') that co-operates with the casing (2) to form the connection channel (132).

7. A dispenser head according to claim 1, in which the core (1) forms a collar (12) that is engaged in the base skirt (22) formed by the casing (2).

8. A dispenser head according to claim 1, in which the dispenser endpiece (24) presents a flat spatula shape.

9. A dispenser head according to claim 1, in which the dispenser orifice is formed by a self-sealing flexible slot (241).

10. A dispenser head according to claim 1, in which the bearing surface (231) slopes, forming an angle lying in the range 40° to 90° relative to the central axis, in such a manner as to intersect the central axis.

11. A dispenser head according to claim 1, in which the dispenser endpiece (24) is flexible, at least in part, in particular at its free end (243).

12. The cosmetic product dispenser according to claim 1, wherein the inlet duct extends completely through the core along the central axis (X).

13. A cosmetic product dispenser device comprising:
a pump having an actuator rod displaceable along a central axis (X) of the actuator rod; and
a dispenser head comprising:
an axial connection sleeve that connects to the actuator rod and defines an inlet duct;
an endpiece comprising a channel connected to the inlet duct, the endpiece further comprising a dispenser orifice at a downstream end of the channel, and wherein the endpiece extends substantially parallel to the central axis (X), and is offset from the central axis (X); and a bearing surface on which axial pressure can be exerted so as to depress the actuator rod;
wherein the bearing surface intersects the central axis (X);
the dispenser head further comprising an inner core and an outer casing, the core being received axially in the casing the central axis (X) and entirely disposed within the casing, the core forming the connection sleeve and part of the channel, the casing forming a base skirt, the dispenser endpiece and a bearing wall defining the bearing surface.

14. The dispenser device according to claim 13, wherein a shape of an inner surface of the outer casing corresponds with a shape of the outer surface of the inner core.

15. The cosmetic product dispenser according to claim 13, wherein the inlet duct extends completely through the core along the central axis (X).

16. A cosmetic product dispenser head for mounting on an actuator rod (33) of a pump (3) that is displaceable down and up along an axis (X), said head comprising an axial connection sleeve (11) for engaging on the actuator rod (33) and defining an inlet duct (113), said head further comprising a dispenser endpiece (24) defining an endpiece channel (142, 242) that is connected to the inlet duct (113) via a connection channel (132), said endpiece (24) including a dispenser orifice (241) that is situated at a downstream end of the endpiece channel, said head further comprising a bearing surface (231) on which axial pressure can be exerted so as to drive in the actuator rod (33), the endpiece (24) extending substantially parallel to said axis (X), and being offset away from the axis, the bearing surface (231) located axially downstream from the connection sleeve (11), intersecting said axis (X), the head further comprising a base skirt (22) that extends around the connection sleeve (11), the endpiece (24) being inscribed within the outline of the base skirt, the endpiece (24) being axially tangential to said base skirt (22);

the cosmetic product dispenser head further comprising an inner core (1), and an outer casing (2), said core being entirely engaged in said casing, the core (1) being received axially in the casing (2) along the central axis (X), the core (1) forming the connection sleeve (11) and part of the connection channel (132), the casing (2) forming the base skirt, the dispenser endpiece (24) and a bearing wall (23) defining the bearing surface (231);
wherein the core (1) forms an axial spout (14) that is engaged in the endpiece (24), a bottom portion (142) of the endpiece channel being formed between the casing (2) and the spout (14); and
wherein the spout (14) includes an axial groove (142') that co-operates with the dispenser endpiece (24) to form the bottom portion (142) of the endpiece channel.

17. A cosmetic product dispenser head for mounting on an actuator rod (33) of a pump (3) that is displaceable down and up along an axis (X), said head comprising an axial connection sleeve (11) for engaging on the actuator rod (33) and defining an inlet duct (113), said head further comprising a dispenser endpiece (24) defining an endpiece channel (142, 242) that is connected to the inlet duct (113) via a connection channel (132), said endpiece (24) including a dispenser orifice (241) that is situated at a downstream end of the endpiece channel, said head further comprising a bearing surface (231) on which axial pressure can be exerted so as to drive in the actuator rod (33), the endpiece (24) extending substantially parallel to said axis (X), and being offset away from the axis, the bearing surface (231) located axially downstream from the connection sleeve (11), intersecting said axis (X), the head further comprising a base skirt (22) that extends around the connection sleeve (11), the endpiece (24) being inscribed within the outline of the skirt, the endpiece (24) being axially tangential to said skirt (22);

the cosmetic product dispenser head further comprising an inner core (1), and an outer casing (2), said core being entirely engaged in said casing, the core (1) being received axially in the casing (2) along the central axis (X), the core (1) forming the connection sleeve (11) and part of the connection channel (132), the casing (2) forming the base skirt, the dispenser endpiece (24) and a bearing wall (23) defining the bearing surface (231);

wherein the core (1) forms a bearing plate (13) into which the duct (113) opens out axially, the connection channel (132) being formed between the plate (13) and the casing (2); and wherein the plate (13) includes a transverse groove (132') that co-operates with the casing (2) to form the connection channel (132).

\* \* \* \* \*